United States Patent
Zavislan et al.

[11] Patent Number: 5,788,639
[45] Date of Patent: Aug. 4, 1998

[54] CONFOCAL IMAGING THROUGH THICK DERMAL TISSUE

[75] Inventors: James M. Zavislan; Jay M. Eastman, both of Pittsford, N.Y.

[73] Assignee: Lucid Technologies, Inc., Henrietta, N.Y.

[21] Appl. No.: 650,684

[22] Filed: May 20, 1996

Related U.S. Application Data

[60] Provisional application No. 60/001,141, Jul. 13, 1995.
[51] Int. Cl.$^6$ ............................................. A61B 5/00
[52] U.S. Cl. ..................................... 600/476; 600/473
[58] Field of Search ........................... 128/633, 664, 128/665; 606/9; 607/88, 89; 356/338, 342, 343

[56] References Cited

U.S. PATENT DOCUMENTS

| | | |
|---|---|---|
| 4,768,874 | 9/1988 | Webb . |
| 4,817,622 | 4/1989 | Pennypacker . |
| 4,991,953 | 2/1991 | Pflibsen . |
| 5,048,904 | 9/1991 | Montagu . |
| 5,120,953 | 6/1992 | Harris . |
| 5,122,653 | 6/1992 | Ohki . |
| 5,321,683 | 6/1994 | Olczack .............................. 369/112 |
| 5,464,436 | 11/1995 | Smith .................................. 606/9 |
| 5,532,874 | 7/1996 | Stein . |

OTHER PUBLICATIONS

Milind Rajadhyaksha et al., "In Vivo Confocal Scanning Laser Microscopy of HumanSkin: Malanin Provides Strong Contrast".The Journal of Investigative Dermatology, vol. 104, No. 6 Jun. 1995.

Small Business Innovation Research Prog; issued Sep. 28, 92; Grant No. SSS–3 (BA) 1 R43 RRo7737–01; awarded by National Center for Research Resources; entitled Confocal Laser Scanning Microscope—Video, Vector & Zoom.

*Primary Examiner*—David M. Shay
*Assistant Examiner*—Bryan K. Yarnell
*Attorney, Agent, or Firm*—K. Lukacher; M. Lukacher

[57] ABSTRACT

A handheld confocal imaging system for in vivo observation of dermal and subdermal tissue allows diagnosis of conditions substantially beneath the surface of the skin. A confocal head has optics which scan the tissue so as to provide images of vertical sections of the tissue. Both two and three dimensional imaging may be provided for diagnosis and location of basal cell carcinomas and melanomas, and so as to enable visualization of tumor borders prior to excision.

35 Claims, 2 Drawing Sheets

1

CONFOCAL IMAGING THROUGH THICK DERMAL TISSUE

This application claims the priority benefit of co-pending provisional application, Ser. No. 60/001,141, filed Jul. 13, 1995.

FIELD OF THE INVENTION

The present invention relates to handheld confocal imaging system for in vivo clinical examinations of dermal and subdermal tissues using non-ionizing radiation, and particularly laser radiation which is of a wavelength capable of penetrating into the skin.

The invention is especially suitable for providing an instrument for dermal pathology applications. The invention is also applicable for visualizing sections in other scattering media than tissue. The invention enables the use of a laser as a source of illumination. The instrument may provide data to image processing computers, which may be programmed to provide high resolution images of dermal sections.

BACKGROUND OF THE INVENTION

Systems have been proposed for viewing the surface areas of the skin or the external surfaces of internal tissue. Viewing without scanning is described in Pennypacker, U.S. Pat. No. 4,817,622, issued Apr. 4, 1989. Examination of internal tissue surfaces by means of beam scanning are proposed in Harris, U.S. Pat. No. 5,120,953, issued Jun. 9, 1992, Ohki, U.S. Pat. No. 5,122,653 issued Jun. 16, 1992, Webb, U.S. Pat. No. 4,768,874 issued Sep. 6, 1988 and Pflibsen, U.S. Pat. No. 4,991,953 issued Feb. 12, 1991. Such proposals have not provided a handheld instrument which is readily usable by a surgeon in clinical examinations for imaging the epidermis and dermis, especially in vertical sections or in horizontal sections at desired depths below the surface of the skin.

SUMMARY OF THE INVENTION

Accordingly, it is the principal object of the present invention to provide and improve clinical dermatological imaging system.

It is another object of the invention to provide an improved confocal imaging system which provides images of dermatological tissues and avoids the need for biopsies to detect the location of such abnormalities as basal cell carcinomas and melanomas.

It is a still further object of the present invention to provide an improved confocal dermatological imaging system which does not require ionizing radiation and may use a laser beam.

It is a still further object of the present invention to provide an improved confocal imaging system which provides in vivo imaging of dermatological tissue both at and below the skin and which may be handheld and which is capable of operating in various scattering media.

It is a still further object of the present invention to provide an improved confocal dermatological imaging system which may use a computer to generate images from data produced by the optics which provides confocal imaging and to display or provide images for further evaluation or computer enhancement.

BRIEF DESCRIPTION OF THE DRAWINGS

The foregoing objects, features and advantages of the invention will become more apparent from a reading of the following description in connection with the accompanying drawings in which.

DETAILED DESCRIPTION OF THE INVENTION

Figure 1:
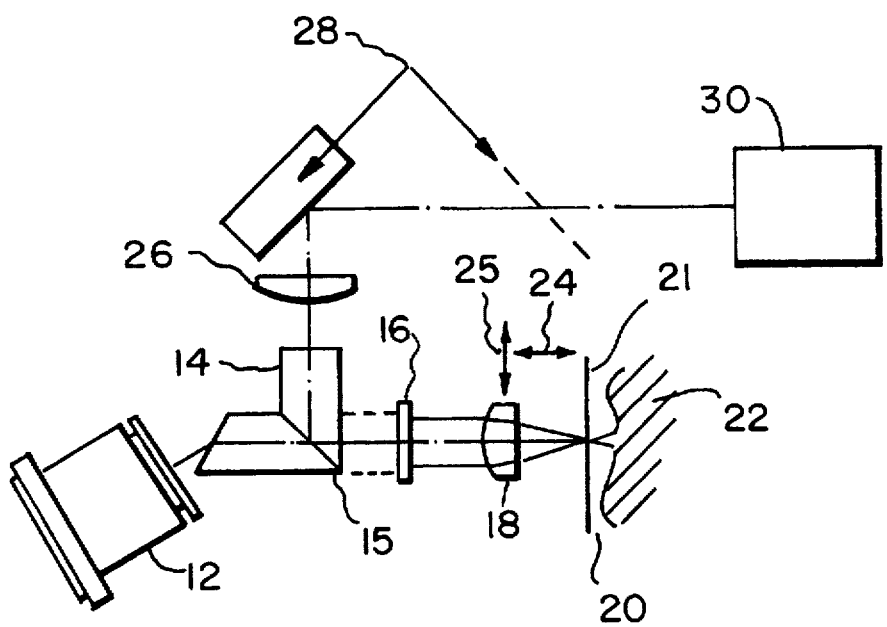
FIG. 1 is schematic diagram of a confocal imaging system embodying the invention.
Figure 1A:
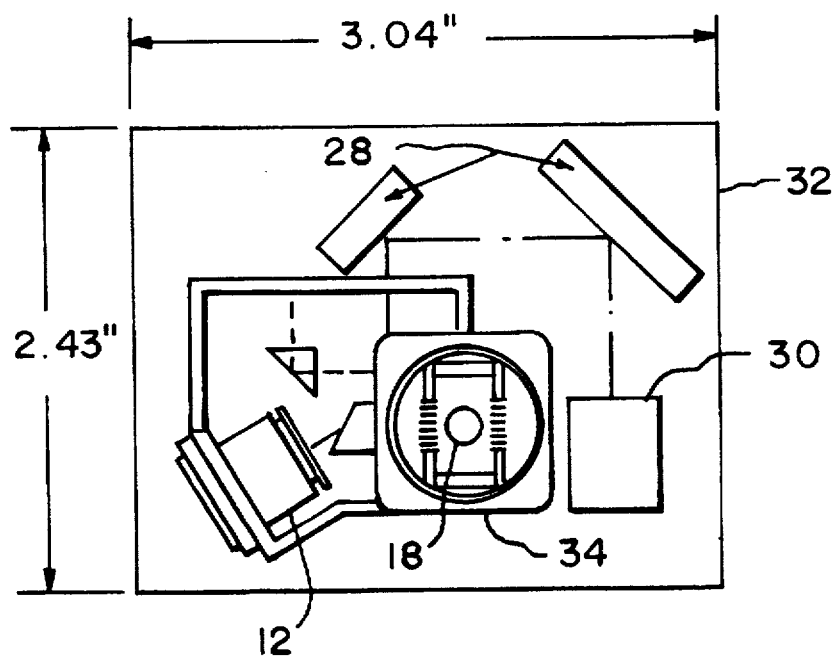
FIG. 1a is a plan view of the head of the system shown in FIG. 1.

Referring to FIG. 1 there is shown a system 10 for in vivo diagnosis of dermatological tissues. The system 10 may be embodied in a handheld head 32 as shown in FIG. 1a and schematically in FIG. 3.

Referring more particularly to FIG. 1 there is shown a system 10 (or instrument) which contains optics of the type which are used in optical data storage heads which are used in recording and reading optical disks. Light from a laser diode, contained in a laser and collimator assembly 12, is collimated by a diffraction limited lens in the assembly 12 and is incident at an oblique angle on a beam splitter assembly 14. Refraction at this oblique angle causes the elliptical laser diode beam to become circular in cross-section. The circular beam passes through the beam splitter assembly 14 and a quarter wave plate 16 and is focused into the tissue 22 via a contact window 20 (a glass window plate) spaced from the sample, specimen or tissue 22 being examined, preferably by an optical contact liquid 21. In the event the sample is viscus or liquid, it may be located in a sample well (not shown).

The circular beam which passes through the beam splitter assembly 14 and the quarter wave plate 16 is focused into the sample by a precision focusing lens 18, which suitably has a numerical aperture of 0.5 and a focal length of 4.3 millimeters. These dimensions and parameters are exemplary and demonstrate that the optical system 10 may be miniaturized so as to be adapted to be handheld.

The quarter wave plate 16 converts the incident linear polarization from the laser in assembly 12 to circular polarization, i.e., the quarter wave plate is oriented 45° to the incident polarization. In other words, the beam from plate 16 is circularly polarized. The focusing lens 18 is movable both in a direction along its optical axis and laterally as indicated by the arrows 24 and 25, respectively. Position mechanical actuators 34 (FIG. 1a) may be used for moving the lens 18, and thereby control position of the focus spot of beam in the sample. These actuators 34 may be similar to those used in optical disk systems. The lens 18 may be mounted on a pair of such mechanical actuators. The actuators 34 provide lateral and vertical scanning of the focused laser beam in the tissue sample.

The focusing lens 18 also collects scattered light reflected from the sample. The amount of coherent light scattered back into the detection system (which includes lens 18, plate 16 and assembly 14) depends upon local variations of the refractive index and the absorption in the immediate neighborhood of the focus spot. This coherent light may be defined as the component of the reflected light having a circular polarization orthogonal to the polarization of the beam focused into the tissue sample. The scattered light is incident to plate 16 and then to beam splitter assembly 14.

The plate 16 converts the coherent component of the scattered light into linear polarization, where beam splitter assembly 14 directs by reflection (or filters) the coherent light component of the scattered light at the beam splitting surface 15 in the beam splitter assembly 14. The reflected light passes through a relay lens 26. The light from relay lens 26 may be reflected from a pair of fold mirrors 28 (See also FIG. 1a). These fold mirrors 28 may be part of the beam splitter assembly 14. The relay lens 26 may also be part of this assembly 14.

The scanned light from the focus spot is reflected from the fold mirrors 28 to a pinhole photodetector assembly 30, which may also be considered part of the detection system. The fold mirrors 28 are used to make the instrument more compact. A prism assembly may alternatively be used, which is part of the beam splitting assembly 14, and allows the samples to be placed face down. This orientation allows gravity to assist in maintaining the sample in a stable viewing position. Maintaining a stable viewing position is also enhanced by the use of the window 20 as shown in FIG. 1.

A top view of the instrument is illustrated in FIG. 1a. Typical dimensions are given in FIG. 1a to illustrate the compacted size of the confocal imaging head 32. The elements in the head 32 may be located on a single board to provide unitized construction. The height of the head may be approximately two inches from the base to the nominal focal point of the focusing lens 18.

By scanning using the mechanical actuators 34 successive lines may be scanned at successive depths to provide images of vertical sections (i.e., along a vertical plane through the tissue sample). If desired the images may be formed from horizontal sections (i.e., along a horizontal plane through the tissue sample) as the lines are scanned horizontally. By tilting the sample, sections at desired angles to the surface of the sample (i.e., along a tilted or non-perpendicular plane) may be formed, such sections may also be formed by moving the lens 18 via actuator 34 as desired angles.

Figure 2:
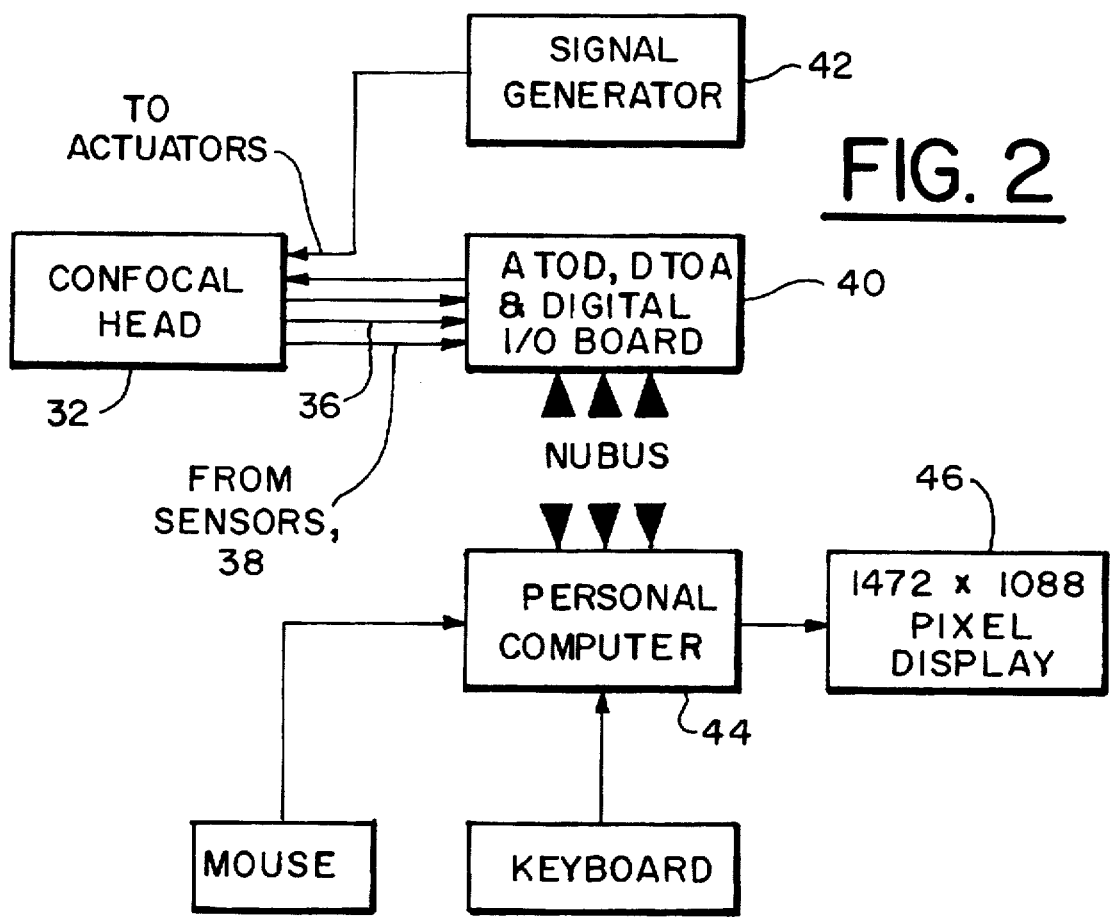
FIG. 2 is a block diagram of the system shown in FIG. 1, and especially the computer control and imaging system for acquisition and processing of the optical image.

Referring to FIG. 2, there is shown a block diagram of the data acquisition and analysis system which is part of the imaging system 10 provided by the invention. The confocal head 32 is the head shown in FIGS. 1 and 1a. The output 36 from the head 32 is the output from the pinhole detector assembly 30. This output 36 is the confocal detector signal. Signals are also provided from sensors 38, namely a lateral position sensor and a vertical position sensor. These signals after amplification and filtering are acquired by a analog to digital converter of a digital I/O board 40. This board 40 may also be on a board with a circuit which provides a digital to analog channel to drive the lateral motion actuator. The vertical scanning actuator is driven from a signal derived from a conventional signal generator 42. The A to D, D to A and digital I/O board 40 is controlled and data is acquired via software in a personal computer 44, such as a Macintosh Quadra 950. Conventional software packages may be used for image analysis and for driving a display 46, which is shown by way of example as a 1472 by 1088 pixel display.

Figure 3:
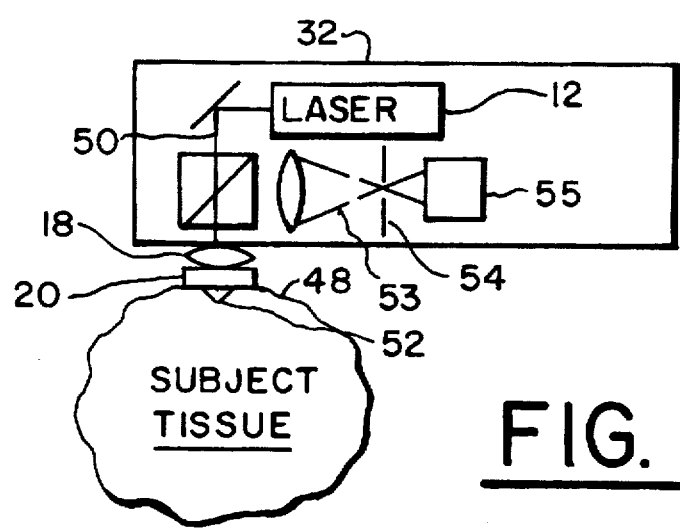
FIG. 3 is a schematic diagram of the handheld confocal imaging system of FIG. 2 in use.

Referring to FIG. 3, there is shown the confocal imaging head 32 contacted against the skin 48 of a subject specimen using a mineral oil as an optical index matching fluid, which is an optical contact liquid 21 (FIG. 1) for reducing undesired reflections of light from the surface of the skin. The force against the skin 48 will be limited to that required to press the skin against the contact window 20 of the head 32. A laser beam 50 which may be relatively low power (e.g., 6.3 milliwatts of optical power) is focused into the dermis of the specimen. The laser is operated at a wavelength capable of penetrating into the skin of the specimen, thus the skin may be considered transparent to the laser wavelength (or in other words, the skin is permeable to electromagnetic radiation of specified frequencies). The depth of focal point or spot 52 is varied from the surface of the stratum corneum to a few millimeters below the surface of stratum corneum. The nominal beam spot size may be, for example, 2.5 micrometers, full width half maximum. The laser spot is scanned laterally across the skin, for example at a rate of 3 to 10 hz. Different laser wavelengths may be selectively used for different resolution. Inasmuch as the energy delivered is proportional to the illuminating flux focused divided by the diameter of the spot, the scan length and the scan rate or frequency, the amount of incident flux is sufficiently low that damage to the specimen is avoided. The light scattered by the tissue is collected and the lights coherent component is re-imaged onto the pinhole aperture 54 of assembly 30, as shown in FIGS. 1 and 1a. The pinhole 54 transmits the coherent light from the focal region of the incident beam 53 to the detector 55 (of assembly 30) where it converts the light into an electrical signal. As the lens 18 scans laterally, the electrical signal is acquired by the computer and stored. Each scan represents a one dimensional trace of the reflectivity and scattering cross section of the dermis at a given level below the surface of the skin 48. A series of scans are made with the focal point positioned at progressively lower depths thereby providing a vertical cross section image of the skin which may be similar to a B-scan ultrasound image. As stated earlier, these scans may also be horizontal to provide a horizontal cross-section, or at an angle to provide an angular cross-section of the skin.

From the foregoing description it will be apparent that there has been provided an embodiment of a confocal imaging system for dermatological pathology applications. Variations and modifications of the herein described system and other applications for the invention will undoubtedly suggest themselves to those skilled in the art. Accordingly, the foregoing description should be taken as illustrative and not in a limiting sense.

What is claimed is:

1. A confocal imaging system for examination of an in-vivo tissue sample having a surface, said system comprising:

a housing which can be hand held;

confocal imaging optics in said housing for focusing below the surface and scanning a focal spot in a plane through the tissue sample extending below said surface;

a source of laser illumination which illuminates the tissue sample through the confocal imaging optics;

means for detecting light returned from the tissue as said spot scans and converting said detected light into electrical signals; and means for processing said signals to provide an image of said tissue sample below said surface.

2. The system of claim 1 wherein said confocal imaging optics further comprises means for collecting and imaging reflected light from the illuminated tissue sample.

3. The system of claim 1 wherein said source is enabled to provide laser illumination at a wavelength transparent to said tissue.

4. The system of claim 1 wherein said confocal imaging optics comprises a lens, and means for moving the position of said lens to enable scanning of said focal spot through the tissue sample.

5. The system of claim 4 wherein said moving means further comprises means for moving said lens in one of different said planes through the tissue sample so as to provide sections from the group consisting of: horizontally spaced sections, angularly spaced sections, and vertically spaced sections.

6. The system of claim 4 wherein said moving means is provided by a plurality of positioning actuators.

7. The system of claim 1 wherein said confocal imaging optics comprises means for converting said laser illumination into circularly polarized light to enable said tissue sample to be illuminated by said circularly polarized light.

8. The system of claim 7 wherein said confocal imaging optics further comprises means for collecting circularly polarized light reflected light from the illuminated tissue sample which is orthogonal to the circularly polarized light which illuminated the tissue sample.

9. The system of claim 1 further comprising a window in said housing through which said confocal imaging optics illuminates said tissue sample, said window having a surface spaced from said tissue sample.

10. The system of claim 9 further comprising an optical index matching fluid located between said surface of said window and said tissue sample.

11. The system of claim 1 wherein said detecting and converting means further comprises a detection system for receiving reflected light from the illuminated tissue sample, said received reflected light having a coherent component.

12. The system of claim 11 wherein said detection system produces, responsive to said coherent component of said received reflected light, electrical signals representative of a section of said tissue sample.

13. The system of claim 12 wherein said processing means further comprises means for collecting data representative of said electrical signals, and means for processing said collected data to display a scan image of said tissue sample based on said collected data.

14. The system of claim 11 wherein said detection system further comprising a photo-detector assembly, and optical elements for relaying said coherent component of said reflected light to said photo-detector assembly, said photo-detector assembly being enabled to convert said coherent component of said reflected light into electrical signals.

15. The system of claim 11 wherein said confocal imaging optics, said detection system, and said source are a unitized construction in said housing.

16. The system of claim 1 wherein said laser illumination from said source is a laser beam, said detecting and converting means further comprises a photo-detector assembly for converting received light into electrical signals, and said confocal imaging optics comprise:

a beam splitter for receiving said laser beam from said source at an oblique angle and providing a circular beam;

a plate incident to said circular beam which polarizes said circular beam to provide a circularly polarized beam;

a lens incident to said circularly polarized beam to focus said circularly polarized beam into said tissue sample and to collect light returned from said tissue sample;

said returned light being incident to said plate and then to said beam splitter; and said beam splitter reflects part of said returned light incident thereto, and said reflected part of said returned light is optically coupled to said photo-detector assembly.

17. The system of claim 16 wherein said returned light from said tissue sample collected by said lens has a component which is circularly polarized orthogonal to the beam focused into the tissue sample, said plate converts the component of the returned light into linearly polarized orthogonal light, and said beam splitter by reflecting part of said returned light filters said component from said returned light.

18. The system of claim 1 wherein said in-vivo tissue is dermal tissue.

19. The system of claim 1 wherein said source of laser illumination is in said housing.

20. The system of claim 1 further comprising a window through which said confocal imaging optics illuminate said tissue sample, said housing and said window being in assembled relationship.

21. The system of claim 1 further comprising a window through which said confocal imaging optics illuminate said tissue sample, said tissue sample and said window being pressed together in contacting relationship during imaging.

22. A method of providing a display of a tissue section, said section being a section of a subject which is located below a surface of tissue, said method comprising the steps of:

directing a laser beam, via confocal optics having a lens, to the tissue;

varying position of said lens to scan a focal spot through said section below the surface;

detecting light returned from the tissue as said spot scans;

converting said light into electrical signals; and processing said signals to provide a display of said section.

23. The method of claim 22 wherein said laser beam operates at a wavelength transparent to the tissue.

24. The method of claim 22 wherein said step of detecting light is responsive to said position of said lens.

25. The method of claim 22 wherein said step of varying the position of said lens further comprises the step of varying the position of said lens to scan along a plane oriented below the surface so as to provide sections from the group consisting of: horizontally spaced sections, angularly spaced sections, and vertically spaced sections.

26. The method of claim 22 wherein said step of directing a laser beam via confocal optics further comprises the steps of converting said laser beam into circularly polarized light, and illuminating said tissue by said circularly polarized light.

27. The method of claim 26 wherein said step of detecting light returned from the tissue further comprises the step of collecting circularly polarized light reflected from the illuminated tissue which is orthogonal to the circularly polarized light which illuminated the tissue.

28. The method of claim 22 wherein said step of directing a laser beam via confocal optics further comprises providing a window having a surface through which said confocal optics directs said laser beam to the tissue, and providing an optical index matching fluid located between said surface of said window and said surface of said tissue to reduce light reflected from the surface of the tissue.

29. The method of claim 22 wherein said step of directing a laser beam via confocal optics having a lens to the tissue further comprises the steps of:

translating said laser beam into a circular beam;

circularly polarizing said circular beam; and focusing with said lens said circularly polarized beam into said tissue.

30. The method of claim 29 wherein said step of detecting light returned from the tissue as said spot scans further comprises the steps of:

collecting with said lens light returned from said tissue, said returned light having a component of circularly polarized light orthogonal to said circularly polarized beam focused into said tissue;

linearly polarizing said component of said returned light; and filtering said linearly polarized component, wherein said converting step is responsive to said filtered linearly polarized component of said returned light.

31. The method of claim 22 wherein said subject is a patient, and said tissue is in-vivo tissue of said patient.

32. The method of claim 31 wherein said in-vivo tissue is located in dermal tissue layers.

33. The method of claim 22 wherein said step of varying position of said lens further comprises the step of varying position of said lens to scan a focal spot over a succession of lines in said section below said surface.

34. The method of claim 22 wherein said directing step further comprises the step of providing a window through which said confocal optics direct said laser beam to the tissue.

35. The method of claim 34 further comprising the step of pressing together said window and the surface of said tissue together into contacting relationship.

* * * * *